(12) United States Patent
Molee

(10) Patent No.: US 6,610,391 B2
(45) Date of Patent: Aug. 26, 2003

(54) ABSORBENT PRODUCT WITH REDUCED REWET PROPERTIES

(75) Inventor: Kenneth John Molee, Suwanee, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 16 days.

(21) Appl. No.: 09/854,502

(22) Filed: May 15, 2001

(65) Prior Publication Data

US 2002/0187322 A1 Dec. 12, 2002

(51) Int. Cl.[7] .............. B32B 7/02; B32B 3/10; A61F 13/20
(52) U.S. Cl. ............. 428/212; 428/131; 428/137; 428/219; 604/372
(58) Field of Search ................ 428/212, 219, 428/131, 137; 604/372

(56) References Cited

U.S. PATENT DOCUMENTS

| | | |
|---|---|---|
| 4,323,069 A | 4/1982 | Ahr et al. |
| 4,842,595 A | 6/1989 | Nakanishi et al. |
| 4,924,084 A | 5/1990 | Lask et al. |
| 5,275,590 A | 1/1994 | Huffman et al. |
| 5,281,207 A | 1/1994 | Chmielewski et al. |
| 5,352,217 A | 10/1994 | Curro |
| 5,415,640 A | 5/1995 | Kirby et al. |
| 5,439,458 A | 8/1995 | Noel et al. |
| 5,522,809 A | 6/1996 | Larsonneur |
| 5,603,607 A | 2/1997 | Kondo et al. |
| 5,603,707 A | 2/1997 | Trombetta et al. |
| 5,643,240 A | 7/1997 | Jackson et al. |
| 5,658,268 A | 8/1997 | Johns et al. |
| 5,763,335 A | 6/1998 | Hermann |
| 5,916,670 A | 6/1999 | Tan et al. |
| 5,941,862 A | 8/1999 | Haynes et al. |
| 6,022,607 A | 2/2000 | James et al. |
| 6,086,950 A | 7/2000 | Masaki et al. |
| 6,107,539 A | 8/2000 | Palumbo et al. |
| 6,123,694 A | 9/2000 | Pieniak et al. |
| 6,171,291 B1 | 1/2001 | Osborn, III et al. |
| 6,176,952 B1 | 1/2001 | Maugans et al. |

Primary Examiner—Cynthia H. Kelly
Assistant Examiner—Lawrence Ferguson
(74) Attorney, Agent, or Firm—Hunton & Williams

(57) ABSTRACT

An absorbent product comprising a topsheet, a secondary absorbent layer, a primary absorbent layer and a backsheet is disclosed. The topsheet preferably is apertured and has a relatively high loft while also having a relatively low open area. The topsheet aids in the fluid flow through the topsheet to the secondary absorbent layer. The secondary absorbent layer absorbs the fluid and acts as a holding reservoir until the primary absorbent layer can absorb the fluid held in the secondary absorbent layer. The absorbent product has been shown to have improved rewet characteristics.

42 Claims, 2 Drawing Sheets

ABSORBENT PRODUCT WITH REDUCED REWET PROPERTIES

BACKGROUND OF INVENTION

1. Field of the Invention

The invention relates to the field of absorbent products having reduced rewet properties, and more particularly, to an absorbent product having particular applicability to feminine hygiene products having reduced rewet properties.

2. Description of the Related Art

Traditionally, layered absorbent articles have included an inner or body facing cover of a porous fabric, an inner liquid absorbing layer or core, and an outer layer of liquid impervious film. In early products, the core was composed entirely of cellulose wadding or pulp, with the bulkiness or dry weight of the core being directly related to the maximum liquid absorption capacity.

More recently, proposals have been advanced to reduce the bulk of the core and to reduce the overall thickness of the absorbent product for several reasons, such as reduced shipping cost and storage space and better conformability of the absorbent article or garment to the body of the user. A reduced absorbent core thickness has been accomplished primarily by increasing the density of the absorbent core and by adding super-absorbent polymer, which is capable of absorbing many times its weight of liquid. These changes, however, have inevitably led to a reduction in the rate of absorption of liquid into the core, resulting in possible runoff and leakage of liquids, and the inability to completely retain the absorbed liquid.

In order to minimize the problems associated with low bulk absorbent articles, additional proposals have been made to employ a high bulk fabric as the upper layer, or to incorporate a transition layer of nonwoven fabric between the outer layer and the core. The purpose of this layer, also known as a sublayer or surge layer, is to hold or retain excess liquid for a time sufficient to allow the core to permanently absorb the liquid.

Various types of fabrics have been used as sublayers, including low density lofty fabrics having a high liquid void volume. These lofty fabrics typically have a porosity of greater than 97 percent and are made from through-air thermally bonded bicomponent fibers to provide a sublayer having a high void volume. Airformed wood pulp also has been used as sublayer material. Traditionally, the topsheets of layered absorbent articles are formed from polymeric fabrics, such as polypropylene and polyethylene spunbonded fabrics. Such topsheets may also comprise an apertured material having openings extending from the surface of the material to the sublayers. Such fabrics are known in the art.

In view of the foregoing considerations, there is a continuing need to provide layered absorbent articles of the compact type that not only are capable of retaining liquid insults to be absorbed by the core, but also are capable of providing good separation and a significantly reduced amount of liquid rewet to the top sheet.

SUMMARY OF THE INVENTION

The present invention relates to a novel compact absorbent product that has been found to provide optimal absorbency while simultaneously decreasing the amount of rewet when compared to other absorbent products. The absorbent product is a unique combination comprising a topsheet, a secondary absorbent layer, a primary absorbent layer and a backsheet. The topsheet is apertured and has a relatively high loft while also having a relatively low open area. The topsheet preferably aids in the fluid flow through the topsheet to the secondary absorbent layer. The secondary absorbent layer absorbs the fluid and preferably acts as a holding reservoir until the primary absorbent layer can absorb the fluid held in the secondary absorbent layer.

These and other features and advantages of this invention will become evident from the following description of the preferred embodiments of this invention, with reference to the accompanying drawings.

DETAILED DESCRIPTION OF THE INVENTION

As used herein, the terms "absorbent article" or "absorbent product" refer to items that absorb and contain fluid discharges and exudates, and more specifically refer to articles that are placed against or in proximity to the body of the wearer to absorb and contain various bodily discharges. A non-exhaustive list of examples of absorbent articles or absorbent products includes diapers, diaper cores, diaper covers, disposable diapers, training pants, feminine hygiene products and adult incontinence products. The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above.

In general terms, an absorbent article of the present invention comprises a layered laminate. The first layer is a liquid permeable apertured film that faces the wearer's body. The second layer is a secondary absorbent layer and the third layer is a primary absorbent layer. The secondary absorbent layer preferably holds fluids until they can be absorbed by the primary absorbent layer, and may also serve to redistribute fluids to other regions of the article. The fourth layer is a liquid impermeable backsheet. It has been found that the unique combination of materials for the topsheet, secondary absorbent layer, and primary absorbent layer that are described herein provides surprising and unexpected rewet performance, when compared to similar products that do not include the combination of the apertured topsheet, secondary absorbent layer, and primary absorbent layer.

Figure 3:
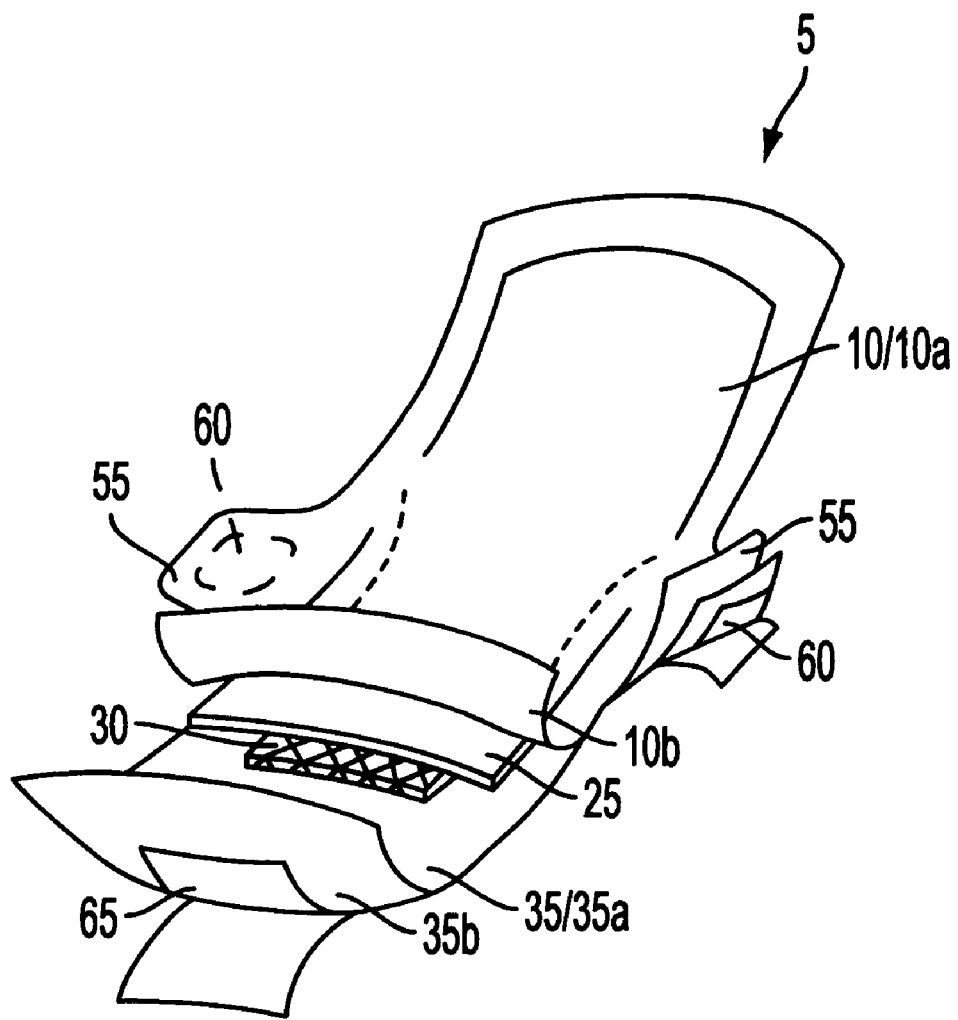
FIG. 3 is a perspective view, with portions in section, of a preferred embodiment of the absorbent product of the present invention.

Referring now to FIG. 3, the present invention relates to an absorbent article 5 comprising a topsheet 10, a secondary absorbent layer 25, a primary absorbent layer 30 and a backsheet 35 that preferably is liquid impermeable. The topsheet 10 preferably comprises a first layer of the absorbent article 5. The topsheet 10 can have a first side 10a that faces the user and a second side 10b opposite the first side 10a, and that is preferably adjacent to at least the secondary absorbent layer 25. The topsheet 10 preferably is fluid pervious. It will be understood that the term "adjacent" as it is used herein, does not necessarily require that the respective layers be immediately adjacent to one another so that their surfaces are in contact with one another. Rather, those skilled in the art will appreciate and recognize that other layers or items may be present between the respective layers or components, such as other layers being present between topsheet 10 and secondary absorbent layer 25.

In a preferred embodiment, the topsheet 10 is comprised of a polyethylene material. As such, the topsheet 10 may be sealed to itself, for example, as a multilayer material, by impulse, resistant, hot air, rotary band, crimp, side-weld, ultrasonic sealing, or any other mechanism capable of sealing the topsheet material. These seals may be made into fin-seals, lap-seals or gusseted.

Figure 1:
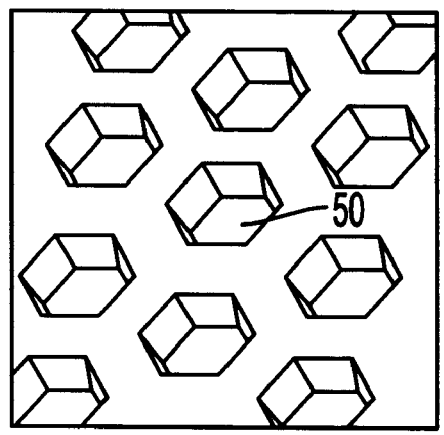
FIG. 1 is a photograph of a preferred embodiment of a first side of the topsheet of an absorbent product, the embodiment being shown approximately 25 times its actual size.
Figure 2:
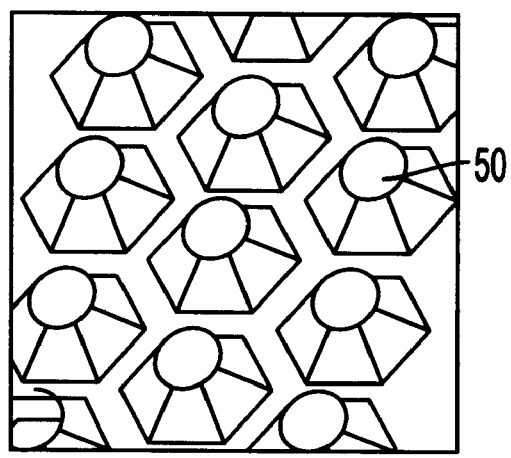
FIG. 2 is a photograph of a second side of the topsheet of a preferred embodiment of the topsheet shown in FIG. 1, the embodiment being shown approximately 25 times its actual size.

As shown in FIG. 1 and FIG. 2, the topsheet 10 preferably has a plurality of apertures 50. In a preferred embodiment, the apertures 50 are microfunnels or cone-like holes wherein the diameter of an aperture 50 on the first side 10a of the topsheet 10 is greater than the diameter of an aperture 50 on the second side 10b of the topsheet 10. The microfunnels provide preferential fluid flow that acts to quickly transport fluid away from the skin of the user and into the secondary absorbent layer 25 while simultaneously inhibiting the reverse flow of these fluids. As such, the apertures 50 aid in fluid flow directly through the topsheet 10 into the secondary absorbent layer 25. This preferred embodiment provides a relatively drier surface in contact with the user than has been previously obtainable, especially when compared to topsheets 10 that are not apertured, or when compared to apertured topsheets 10 in combination with a single absorbent layer. The topsheet 10 preferably aids in the fluid flow through the topsheet 10 to the secondary absorbent layer 25. The secondary absorbent layer 25 absorbs the fluid and preferably acts as a holding reservoir until the primary absorbent layer 30 can absorb the fluid held in the secondary absorbent layer 25.

In another preferred embodiment of the present invention, each microfunnel extends away from the body of the user toward the secondary absorbent layer 25. The cone axis preferably is at about a 90° angle to the plane of the topsheet 10 although other angles are contemplated herein. Preferably, the apertures 50 of the first side 10a of the topsheet 10 are connected to apertures of the second side 10b of the topsheet 10 by tapered capillaries, whereby the tapered capillaries are substantially perpendicular to the first and second sides (10a, 10b) of the topsheet 10. these tapered capillaries preferably allow the free transfer of fluids from the first side 10a of the topsheet 10 into the secondary absorbent layer 25, while inhibiting the reverse flow of fluids.

The apertures 50 of the topsheet 10 of the present invention may be of substantially the same size and shape on the first side 10a and on the second side 10b of the topsheet 10. The apertures 50 may be geometric or isometric shapes. For example, the apertures 50 may have, without limitation, the geometric or isometric shapes of tapered capillaries, slits, funnels or cylinders. In a preferred embodiment, the apertures 50 of the first side 10a of the topsheet 10 are hexagonal. The apertures 50 may also be varied in size and frequency to suit the particular viscosity, density, mass and flow rates of the fluid to be absorbed. For example, the apertures 50 may have a different size and frequency for urine than for menstrual flow. In a preferred method of manufacturing the topsheet 10, the apertures 50 are formed by heating a polyethylene film and then subjecting it to a vacuum such that the microfunnels are formed downward so that the diameter of a microfunnel on the first side 10a of the topsheet 10 is wider than the diameter of the microfunnel on the second side 10b.

The first side 10a or user facing side of the topsheet 10 preferably is relatively smooth. The first side 10a has a higher surface contact area and lower co-efficient of friction than the second side 10b. The first side 10a of the topsheet 10 may have a film-like appearance and tactile impression. The second side 10b, or side that faces the secondary absorbent layer 25, preferably is relatively rough. The second side 10b can have a lower surface contact area than the first side 10a. In a preferred embodiment, the microfunnels of the present invention retain a memory so that the microfunnels bounce back and remain functional after they are compressed.

The apertures 50 of the topsheet 10 provide a relatively high loft or embossed thickness. This relatively high loft has the ability to contain high void volume within the funnels and, as such, contributes to the improved runoff and rewet properties. In a preferred embodiment, the topsheet 10 has a loft or embossed thickness from the first side 10a to the second side 10b of from about 10 mils (i.e., 0.01 inch or 254 microns) to about 38 mils. In a more preferred embodiment, the topsheet 10 has a loft of about 16 mils to about 30 mils. In a most preferred embodiment, the topsheet 10 has a loft of about 20 mils to about 25 mils. It also is preferred in the present invention that the topsheet 10 has a loft from the first side 10a to the second side 10b from about 100 $\mu$m to about 900 $\mu$m. More preferably, the topsheet has a loft from the first side 10a to the second side 10b of from about 250 $\mu$m to about 600 $\mu$m, and most preferably, from about 400 $\mu$m to about 600 $\mu$m.

In an embodiment of the invention, the topsheet 10 can have an open area of from about 2% to about 80%, preferably from about 5% to about 30%, and more preferably, from about 6% to about 26% of the overall area of the topsheet 10. In a most preferred embodiment, the topsheet 10 has an open area of about 16% of the overall area of the topsheet 10. Preferably, the topsheet 10 has a nominal hole diameter of about 4 mils to about 36 mils. More preferably, the topsheet 10 has a nominal hole diameter of about 10 mils to about 30 mils. Most preferably, the topsheet 10 has a nominal hole diameter of about 20 mils.

In a preferred embodiment, the topsheet 10 has a hole density of about 110 holes per square inch to about 990 holes per square inch. In a more preferred embodiment, the topsheet 10 has a hole density of about 275 holes per square inch to about 825 holes per square inch. In a most preferred embodiment, the topsheet 10 has a hole density of about 550 holes per square inch. Preferably, the topsheet 10 has a porosity from about 90 cfm/inch$^2$ (i.e., 90 cubic feet per minute per square inch) to about 990 cfm/inch$^2$. More preferably, the topsheet 10 has a porosity from about 225 cfm/inch$^2$ to about 825 cfm/inch$^2$. Most preferably, the topsheet 10 has a porosity from about 450 cfm/inch$^2$ to about 550 cfm/inch$^2$. In a preferred embodiment, the topsheet 10 has a drain rate of about 2 oz/sec/in$^2$ to about 24 oz/sec/in$^2$. In a more preferred embodiment, the topsheet 10 has a drain rate of about 6 oz/sec/in$^2$ to about 20 oz/sec/in$^2$. In a most preferred embodiment, the topsheet 10 has a drain rate of about 11 oz/sec/in$^2$ to about 13 oz/sec/in$^2$. Those skilled in the art are capable of determining or measuring the properties of topsheet 10, including the open area, nominal hole density, porosity, and drain rate. In addition, a skilled artisan is capable of making a topsheet 10 having the preferred properties described herein. Apertured films having a variety of the dimensions and physical properties mentioned above are commercially available from Tredegar Film Products, a corporation headquartered in Richmond, Va. These apertured films are particularly preferred for use as a topsheet 10 in the present invention.

Referring to FIG. 3, the secondary absorbent layer 25 preferably is positioned adjacent to at least the topsheet 10. The secondary absorbent layer 25 acts as an acquisition layer. The secondary absorbent layer 25 therefore preferably serves to immediately capture fluid as it passes through the topsheet 10, and to hold the fluid in reserve until it can be absorbed by the primary absorbent layer 30.

Examples of suitable materials that may be used as components in the secondary absorbent layer 25 include, without limitation, cellulose fibers, cellulose acetate fibers, rayon fibers, Courtauld's LYOCEL fibers, polyacrylonitrile fibers, surface modified (hydrophilic) polyester fibers, surface modified polyolefin/polyester bicomponent fibers, cotton fibers or blends thereof. Preferably, the secondary absorbent layer 25 comprises a cellulosic fiber. In a preferred embodiment, the secondary absorbent layer 25, or components thereof, may be air-laid. In another preferred embodiment, the secondary absorbent layer 25 is held together with a latex binder. The secondary absorbent layer 25 may additionally be comprised of other additives.

In one embodiment of the present invention, the secondary absorbent layer 25 has a basis weight from about 40 g/m$^2$ to about 120 g/m$^2$. In a preferred embodiment of the present invention, the secondary absorbent layer 25 has a basis weight of from about 60 g/m$^2$ to about 100 g/m$^2$. In a more preferred embodiment of the present invention, the secondary absorbent layer 25 has a basis weight of from about 70 g/m$^2$ to about 90 g/m$^2$. In a most preferred embodiment of the present invention, the secondary absorbent layer 25 has a basis weight of about 80 g/m$^2$. In one embodiment, the basis weight is uniform throughout the secondary absorbent layer 25. However, in another embodiment, the basis weight may vary along the longitudinal or transverse dimensions, or both dimensions, of the absorbent article 5. A skilled artisan will be able to select or manufacture a secondary absorbent layer 25 as described herein, using the guidelines provided herein.

FIG. 3 illustrates the secondary absorbent layer 25 as having a greater width than the primary absorbent layer 30. However, in another preferred embodiment, the width of the primary absorbent layer 30 may be the same as the width of the secondary absorbent layer 25. Additionally, in a preferred embodiment, the width of the primary absorbent layer 30 may be greater than the width of the secondary absorbent layer 25. Further, the length of the primary absorbent layer 30 may be less than, the same as, or greater than the length of the secondary absorbent layer 25. It is preferred that the length of the primary absorbent layer 30 be greater than the length of the secondary absorbent layer 25.

Referring to FIG. 3, the primary absorbent layer 30 preferably is positioned adjacent to the secondary absorbent layer 25. Again, the term adjacent does not necessarily require that the respective layers be immediately adjacent to one another so that their surfaces are in contact with one another. Rather, those skilled in the art will appreciate and recognize that other layers or items may be present between the respective layers or components.

The primary absorbent layer 30 preferably is a composite that absorbs and holds the fluid that has been initially captured by the secondary absorbent layer 25. In a preferred embodiment of the present invention, the primary absorbent layer 30 is a composite of fluff pulp material and superabsorbent polymer (SAP), which may be encased in a tissue layer to minimize loss of absorbent material. Composites of fluff pulp and SAP are known as engineered absorbent material (EAM), and an example is disclosed in U.S. Pat. No. 5,916,670 issued to Tan et al., the disclosure of which is hereby incorporated by reference in its entirety. The tissue layer may be of bleached wood pulp or any other suitable material.

In a preferred embodiment, the EAM consists of a fluff pulp of cellulosic fibers and a SAP of salts of crosslinked polyacrylic acid incorporated into a hydrogen bonded air laid structure. Such an EAM is available under the trade name NovaThin from Rayonier, Inc., a company incorporated in North Carolina. The SAP utilized in the present invention is generally capable of absorbing from about 10 to about 50 times its weight in fluid. In a preferred embodiment, the primary absorbent layer 30 includes a composite having about 10% to about 60% by weight of SAP, about 40% to about 86% by weight of pulp, and about 4% by weight of tissue, based on the entire weight of the composite. In a more preferred embodiment, the primary absorbent layer 30 contains SAP in an amount of about 30% by weight. Skilled artisans will be able to select or manufacture a primary absorbent layer 30 as described herein, using the guidelines provided herein.

Referring to FIG. 3, a fourth layer of the absorbent article of the present invention comprises a backsheet 35. The backsheet 35 has a first side 35a that preferably is positioned adjacent to at least the primary absorbent layer 30. Again, the term adjacent does not necessarily require that the respective layers be immediately adjacent to one another so that their surfaces are in contact with one another. The backsheet 35 has a second side 35b opposite the first side 35a, and that preferably faces a garment of the user. The backsheet 35 preferably is liquid impermeable and functions to prevent liquid penetration from the absorbent article 5 to the garment of the user. In a preferred embodiment of the present invention, the backsheet 35 is a polyethylene film.

In a preferred embodiment, the topsheet 10 and backsheet 35 extend beyond the edges of the secondary absorbent layer 25 and the primary absorbent layer 30. The topsheet 10 and backsheet 35 then can be sealed to one another around the periphery to enclose the secondary absorbent layer 25 and the primary absorbent layer 30. The present invention encompasses an embodiment wherein the periphery of the absorbent product 5 forms a pair of wings 55. The pair of wings 55 may be folded over the edge of the garment to secure the absorbent article 5 to the garment. The pair of wings 55 formed by the periphery may also comprise a flap attachment member 60. The flap attachment member 60 may be used to join the wings 55 to the garment of the user. Further, the second side 35b of the backsheet 35 may have an adhesive attachment member 65 for securing the absorbent product 5 to the garment of the user. Preferably, the absorbent product 5 is thin in order to improve comfort.

In the present invention, it is preferred that the absorbent articles have a third insult rewet value for a third 3 ml insult of ASTM 1670 synthetic blood of less than about 1.5 grams, preferably less than about 1.0 grams, and even more preferably, less than about 0.75 grams. The third insult rewet value can be determined in accordance with the following procedure.

Mark the center of the absorbent product as the insult point. Weigh a strikethrough plate with two brass rings, and place the strikethrough plate with the two brass rings on the insult point. Strikethrough plates with two brass rings are conventional in the art. Using a disposable liquid transfer pipette, dispense about 3 ml of ASTM 1670 synthetic blood (or about 10 ml of 1% saline solution, or about 10 ml of ASTM synthetic urine) into the strikethrough plate, and then remove the strikethrough plate with two brass rings after the liquid has been absorbed. Filter paper can then be weighed to obtain its dry weight, and ten minutes after the strikethrough plate has been removes, the filter paper can be placed on the insult point and a weight producing about 0.5 psi placed on top of the filter paper. the wet filter paper can then be removed and weighed to obtain the wet weight of the filter paper. The first insult rewet value is obtained by simply subtracting the dry weight of the filter paper from the wet weight of the filter paper. These procedures are then repeated using the same absorbent product for a second insult and a third insult to obtain the third insult rewet measurement.

It is also preferred in the invention that the absorbent article have a third insult rewet value for a third 10 ml insult of 1.0% saline solution of less than about 4.50 grams, preferably less than about 3.30 grams, and more preferably less than about 2.5 grams.

Through experimentation and testing, it has been found that the unique combination of materials provided by the present invention, specifically those used to make the topsheet, the secondary absorbent layer, and the primary absorbent layer, provides unexpectedly improved and exceptional dryness following multiple liquid insults when compared to other commercially available absorbent products. More specifically, the combination of the particular apertured film topsheet of the present invention with the secondary and primary absorbent layers described herein, provides unexpectedly superior results when compared to similar products that do not include the combination of apertured topsheet, secondary absorbent layer, and primary absorbent layer. The following examples demonstrate the improved efficacy of the present invention with respect to rewet characteristics.

EXAMPLE 1

For the first Example, an absorbent article of the present invention was compared with similar commercially available products to determine their relative resistances to synthetic blood rewet. The Always Ultra Maxi product and the CVS Maxi Ultrathin both use an apertured topsheet. Unlike the present invention, however, the absorbent layer of each of these products comprises an airlaid material having super absorbent polymer distributed within it using little or no adhesives or other means to fix the SAP in place, and with relatively little mechanical intermixing of the SAP and the airlaid material.

The absorbent products listed in Table 1 were adhered to a mat. The center of each absorbent product was located and marked as the insult point. A strikethrough plate with two brass rings was weighed. Using a disposable liquid transfer pipette, 3 ml of ASTM 1670 synthetic blood was obtained from the graduated cylinder. The strikethrough plate with two brass rings was placed on the insult point. The ASTM 1670 synthetic blood was dispensed from the disposable liquid transfer pipette into the strikethrough plate. The strikethrough plate with two brass rings was then removed from the insult point. Filter paper weighing about 12 g was weighed to obtain its exact dry weight. Ten minutes after the strikethrough plate with two brass rings had been removed, the filter paper was placed on the insult point and a weight producing about 0.5 psi was placed on top of the filter paper. Two minutes later, the weight and filter paper were removed from the insult point. The wet filter paper was then weighed to obtain its wet weight. The rewet result was obtained by subtracting the dry weight of the filter paper from the wet weight of the filter paper. These procedures were then repeated for a second insult using filter paper weighing about 15 g and for a third insult using filter paper weighing about 20 g.

Table 1 provides the results obtained using the above procedure:

TABLE 1

| Absorbent Product | Rewet (g) | | |
|---|---|---|---|
| | $1^{st}$ Insult | $2^{nd}$ Insult | $3^{rd}$ Insult |
| Present Invention | 0.01 | 0.11 | 0.51 |
| Always Ultra Maxi (with flexi-wings) - New Quilted | 0.05 | 1.19 | 2.05 |
| CVS Maxi Ultrathin (with trim wings) - Apertured Topsheet | 0.90 | 1.25 | 1.70 |

These data demonstrate that the present invention provides surprising and unexpected results when compared to conventional absorbent products, even those having similar apertured topsheets, but different absorbent layers. Specifically, the absorbent article of the invention provides significantly better rewet performance, especially at the second and third insults.

EXAMPLE 2

For the second Example, an absorbent article of the present invention was compared with similar commercially available products to determine their relative resistances to saline solution rewet. The Always Ultra Maxi product and the Kendall Confab store brand product both use an apertured topsheet. Unlike the present invention, however, the absorbent layer of each of these products comprises an airlaid material having super absorbent polymer distributed within it using little or no adhesives or other means to fix the SAP in place, and with relatively little mechanical intermixing of the SAP and the airlaid material.

The absorbent products listed in Table 2 were adhered to a mat. The center of each absorbent product was located and marked as the insult point. A strikethrough plate with two brass rings was weighed. Using a disposable liquid transfer pipette, 10 ml of 1.0% saline solution was obtained from the graduated cylinder. The strikethrough plate with two brass rings was placed on the insult point. The saline solution was dispensed from the disposable liquid transfer pipette into a graduated cylinder, then poured into the strikethrough plate. When the saline solution was absorbed into the absorbent product, the strikethrough plate with two brass rings was then removed from the insult point. Filter paper weighing about 12 g was weighed to obtain its exact dry weight. Ten minutes after the strikethrough plate with two brass rings had been removed, the filter paper was placed on the insult point and a weight producing about 0.5 psi was placed on top of the filter paper. Two minutes later, the weight and filter paper were removed from the insult point. The wet filter paper was then weighed to obtain its wet weight. The rewet result was obtained by subtracting the dry weight of the filter paper from the wet weight of the filter paper. These procedures were then repeated for a second insult using filter paper weighing about 15 g and for a third insult using filter paper weighing about 20 g.

Table 2 provides the results obtained using the above procedure:

TABLE 2

| Absorbent Product | Rewet (g) | | |
| --- | --- | --- | --- |
| | 1st Insult | 2nd Insult | 3rd Insult |
| Present Invention | 0.05 | 0.04 | 2.20 |
| Always Ultra Maxi (with flexi-wings) - New Quilted | 0.23 | 4.27 | 7.35 |
| Store Brand (produced by Kendall Confab) | 0.05 | 2.85 | 4.65 |

These data demonstrate that the present invention provides surprising and unexpected results when compared to conventional absorbent products.

Although the present invention has been described in terms of particularly preferred embodiments, it is not limited to these embodiments. Alternative embodiments and modifications that would still be encompassed by the invention may be made by those skilled in the art, particularly in light of the foregoing teachings. Therefore, the following claims are intended to cover any alternative embodiments, modifications or equivalents that may be within the spirit and scope of the invention.

I claim:

1. An absorbent article comprising:
   a first layer comprising a liquid permeable film having a plurality of apertures, the first layer having a first side facing the body of a user and a second side opposite the first side;
   a second layer positioned beneath the first layer, the second layer comprising cellulosic fibers and a latex binder;
   a third layer positioned beneath the second layer, the third layer comprising a composite of cellulosic fiber and super-absorbent polymer (SAP);
   a fourth layer comprising a liquid impermeable backsheet comprising a first backsheet side positioned beneath the third layer; and
   wherein the absorbent article has a third insult rewet value for 3 ml of ASTM 1670 synthetic blood of less than about 0.75 grams.

2. The absorbent article of claim 1, wherein each of the apertures of the first layer has a diameter on the first side that is greater than the diameter on the second side.

3. The absorbent article of claim 1, wherein the composite contains SAP in an amount from about 10% to about 60% by weight of the composite.

4. The absorbent article of claim 1, wherein the fourth layer further comprises a second backsheet side positionable against a garment of a user.

5. The absorbent article of claim 4, wherein the second side of the fourth layer has an adhesive for joining the absorbent article to the garment of the user.

6. The absorbent article of claim 1, wherein the fourth layer and the first layer extend beyond the edge of the second and third layers and are sealed to one another around the periphery of the absorbent article.

7. The absorbent article of claim 6, wherein the periphery of the absorbent article forms a pair of wings configured to be positioned over the edge of a garment of a user.

8. The absorbent article of claim 7, wherein the wing comprises a flap attachment member for joining the wing to the garment of the user.

9. The absorbent article of claim 1, wherein the first layer has a loft from the first side to the second side from about 100 $\mu$m to about 900 $\mu$m.

10. The absorbent article of claim 1, wherein the first layer has a loft from the first side to the second side from about 250 $\mu$m to about 750 $\mu$m.

11. The absorbent article of claim 1, wherein the first layer has a loft from the first side to the second side from about 400 $\mu$m to about 600 $\mu$m.

12. The absorbent article of claim 1, wherein the first layer has an open area from about 5% to about 30% of the overall area of the first layer.

13. The absorbent article of claim 1, wherein the cellulosic fibers of the second layer are air-laid.

14. The absorbent article of claim 1, wherein the second layer has a basis weight from about 40 g/m$^2$ to about 120 g/m$^2$.

15. The absorbent article of claim 1, wherein the second layer has a basis weight from about 60 g/m$^2$ to about 100 g/m$^2$.

16. The absorbent article of claim 1, wherein the second layer has a basis weight from about 70 g/m$^2$ to about 90 g/m$^2$.

17. The absorbent article of claim 1, wherein the first side of the first layer exhibits a fiber-like appearance and tactile impression.

18. The absorbent article of claim 1, wherein the length of the third layer is greater than the length of the second layer.

19. The absorbent article of claim 1, wherein the apertures comprise tapered capillaries.

20. The absorbent article of claim 19, wherein the tapered capillaries are substantially perpendicular to the first and second sides of the first layer.

21. The absorbent article of claim 19, wherein the tapered capillaries allow the free transfer of fluids from the first side of the first layer into the second layer, while inhibiting the reverse flow of the fluids.

22. An absorbent article comprising:
   a first layer comprising a liquid permeable film having a plurality of apertures, the first layer having a first side facing the body of a user and a second side opposite the first side;
   a second layer positioned beneath the first layer, the second layer comprising cellulosic fibers and a latex binder;
   a third layer positioned beneath the second layer, the third layer comprising a composite of cellulosic fiber and super-absorbent polymer (SAP);
   a fourth layer comprising a liquid impermeable backsheet comprising a first backsheet side positioned beneath the third layer; and
   wherein the absorbent article has a third insult rewet value for 10 ml of 1.0% saline solution of less than about 3.30 grams.

23. The absorbent article of claim 22, wherein each of the apertures of the first layer has a diameter on the first side that is greater than the diameter on the second side.

24. The absorbent article of claim 22, wherein the composite contains SAP in an amount from about 10% to about 60% by weight of the composite.

25. The absorbent article of claim 22, wherein the fourth layer further comprises a second backsheet side positionable against a garment of a user.

26. The absorbent article of claim 25, wherein the second side of the fourth layer has an adhesive for joining the absorbent article to the garment of the user.

27. The absorbent article of claim 22, wherein the fourth layer and the first layer extend beyond the edge of the second and third layers and are sealed to one another around the periphery of the absorbent article.

28. The absorbent article of claim 27, wherein the periphery of the absorbent article forms a pair of wings configured to be positioned over the edge of a garment of a user.

29. The absorbent article of claim 28, wherein the wing comprises a flap attachment member for joining the wing to the garment of the user.

30. The absorbent article of claim 22, wherein the first layer has a loft from the first side to the second side from about 100 µm to about 900 µm.

31. The absorbent article of claim 22, wherein the first layer has a loft from the first side to the second side from about 250 µm to about 750 µm.

32. The absorbent article of claim 22, wherein the first layer has a loft from the first side to the second side from about 400 µm to about 600 µm.

33. The absorbent article of claim 22, wherein the first layer has an open area from about 5% to about 30% of the overall area of the first layer.

34. The absorbent article of claim 22, wherein the cellulosic fibers of the second layer are air-laid.

35. The absorbent article of claim 22, wherein the second layer has a basis weight from about 40 g/m$^2$ to about 120 g/m$^2$.

36. The absorbent article of claim 22, wherein the second layer has a basis weight from about 60 g/m$^2$ to about 100 g/m$^2$.

37. The absorbent article of claim 22, wherein the second layer has a basis weight from about 70 g/m$^2$ to about 90 g/m$^2$.

38. The absorbent article of claim 22, wherein the first side of the first layer exhibits a fiber-like appearance and tactile impression.

39. The absorbent article of claim 22, wherein the length of the third layer is greater than the length of the second layer.

40. The absorbent article of claim 22, wherein the apertures comprise tapered capillaries.

41. The absorbent article of claim 40, wherein the tapered capillaries are substantially perpendicular to the first and second sides of the first layer.

42. The absorbent article of claim 40, wherein the tapered capillaries allow the free transfer of fluids from the first side of the first layer into the second layer, while inhibiting the reverse flow of the fluids.

* * * * *